United States Patent [19]
Kroll

[11] Patent Number: 5,366,484
[45] Date of Patent: Nov. 22, 1994

[54] SHORT-PULSE CARDIOVERSION SYSTEM FOR AN IMPLANTABLE CARDIOVERTER DEFIBRILLATOR

[75] Inventor: Mark W. Kroll, Minnetonka, Minn.

[73] Assignee: Angeion Corporation, Plymouth, Minn.

[21] Appl. No.: 866,460

[22] Filed: Apr. 9, 1992

[51] Int. Cl.$^5$ .............................................. A61N 1/39
[52] U.S. Cl. ....................................................... 607/5
[58] Field of Search ........................................ 607/5, 7

[56] References Cited

U.S. PATENT DOCUMENTS

| | | | |
|---|---|---|---|
| 3,747,605 | 7/1973 | Cook | 607/8 |
| 4,727,877 | 3/1988 | Kallok | 607/5 |
| 4,823,796 | 4/1989 | Benson | 607/7 |
| 4,964,406 | 10/1990 | Carroll et al. | 607/5 |
| 5,014,697 | 5/1991 | Pless et al. | 607/7 |
| 5,179,945 | 1/1993 | Hofweggn et al. | 607/5 |
| 5,201,865 | 4/1993 | Kuehn | 607/8 |
| 5,230,336 | 7/1993 | Fain et al. | 607/7 |

OTHER PUBLICATIONS

A. C. Guyton and J. Satterfield, "Factors concerned in defibrillation of the heart, particularly through the unopened chest," *Am J of Physiology*, vol. 167, pp. 81, 1951.

J. C. Schuder, G. A. Rahmoeller, and H. Stoeckle, "Transthoracic ventricular defilbrillation with triangular and trapezoidal waveforms," *Circ Res*, vol. 19, pp. 689–694, Oct. 1966.

W. A. Tacker, L. A. Geddes, J. McFarlane, et al., "Optimum current duration for capacitor-discharge defibrillation of canine ventricles," *J Applied Physiology*, vol. 27 #4, pp. 480–483, Oct. 1969.

J. C. Schuder, H. Stoeckle, J. A. Wes, et al., "Transthoracic ventricular defibrillation in the dog with truncated and untruncated exponential stimuli," *IEEE Trans. Biom. Eng.*, vol. BME-18 #6, pp. 410–415, Nov. 1971.

G. Weiss, "Sur la possibilite' de rendre comparable entre eux les appareils survant a l'excitation electrique," *Arch. de Biol.*, vol. 35, pp. 413–446, 1901.

J. D. Bourland, W. A. Tacker, and L. A. Geddes, "Strength duration curves for trapezoidal waveforms of various tilts for transchest defibrillation in animals," *Med. Instr.*, vol. 12 #1, pp. 38–41, 1978.

J. D. Bourland, W. A. Tacker, L. A. Geddes, et al., "Comparative efficacy of damped sine wave and square wave current for transchest ventricular defibrillation in animals," *Medical Instrum.*, vol. 12 #1, pp. 42–45.

J. A. Pearce, J. D. Bourland, W. Neilsen, et al., "Myocardial stimulation with ultrashort duration current pulses," *PACE*, vol. 5, pp. 52–58, Jan.-Feb. 1982.

P. S. Chen, P. D. Wolf, and F. J. Claydon, "The potential gradient field created by epicardial defibrillation electrodes in dogs," *Circulation*, vol. 74, pp. 626–635, Sep. 1986.

*Primary Examiner*—William E. Kamm
*Attorney, Agent, or Firm*—Patterson & Keough

[57] ABSTRACT

The present invention determines mathematically the optimum pulse duration, d, for a truncated capacitor-discharge waveform employed for cardioversion. The present invention comprehends the system time constant, RC, where R is tissue resistance and C is the value of the capacitor being discharged, and also the cardioversion chronaxie, $d_c$, defined by Lapicque, which is a characteristic time associated with the stimulation of heart tissue. The present invention determines the optimum pulse duration to be roughly the average of RC and $d_c$, appreciably smaller than the value employed in the prior art. The optimized-pulse of the present invention can be applied to a monophasic waveform, or to the first phases of biphasic waveforms. The second phase can be specified to have equal or lesser duration than the first. The process of the present invention can also be applied to the first phases of multiphasic waveforms. Pulse duration can be controlled by sensing duration directly, or by sensing tilt. When energy delivered to the heart is taken to be constant, and the waveform is optimized on that basis, then the waveform has a very short duration, approximating the chronaxie of the myocardial tissue, and the waveform approximates a rectangular pulse.

31 Claims, 3 Drawing Sheets

SHORT-PULSE CARDIOVERSION SYSTEM FOR AN IMPLANTABLE CARDIOVERTER DEFIBRILLATOR

CROSS REFERENCES TO CO-PENDING APPLICATIONS

The present application is related to a co-pending application filed in the United States Patent and Trademark Office on Feb. 18, 1992, Ser. No. 07/835,836, entitled "Optimal Pulse Defibrillator", which is assigned to the assignee of the present invention and the disclosure of which is hereby incorporated by reference in the present application.

BACKGROUND OF THE INVENTION

1. Field of the Invention

The present invention relates generally to cardioversion, specifically tachycardia-termination methods, and more particularly, to truncated and optimum-duration capacitance-discharge pulses comprehending the natural time constants of the system and of the heart.

2. Description of the Prior Art

Implantable cardioverter-defibrillator (ICD) systems now on the market and in use for clinical studies employ capacitors of 120 to 180 microfarads to deliver the defibrillation pulse. The system uses the same capacitor to deliver a cardioversion pulse, and typically, use the same pulse duration for cardioversion as for defibrillation. But because the energy employed for cardioversion is some four to twenty times less than for defibrillation, the voltage in the former case is correspondingly smaller. Low voltages in the later portions of a pulse are known, however, to be ineffective in terminating tachycardia, and even to induce fibrillation. It is worthwhile to provide some background for this observation.

Defibrillation, or causing the cessation of chaotic and uncoordinated contraction of the ventricular myocardium by application of an electrical direct current and voltage, in its most primitive form goes back to the last century. [J. L. Prevost and F. Batelli, "Sur Quelques Effets des Descharges Electriques sur le Couer des Mammifers, "Comptes Rendus Hebdomadaires des Seances de L'Acadmie des Sciences, Vol. 129, p. 1267, 1899.] Because of the large currents required for defibrillation, large-area electrodes are employed. [A. C. Guyton and J. Satterfield, "Factors Concerned in Defibrillation of the Heart, Particularly through the Unopened Chests," Am. J. of Physiology, Vol 167, p. 81, 1951.]

For reasons of simplicity and compactness, capacitor-discharge systems are almost universally used in defibrillation. The discharge of a capacitor C through a resistance R results in a curve of voltage versus time, and hence, of current versus time as well, that is a declining exponential function, with a characteristic time given by the product RC. But it has also been recognized for some time that the long-duration, low-amplitude "tail" of the capacitor-discharge pulse is detrimental. [J. C. Schuder, G. A. Rahmoeller, and H. Stoeckle, "Transthoracic Ventricular Defibrillation with Triangular and Trapezoidal Waveforms," Circ. Res., Vol 19, p. 689, October 1966; W. A. Tacker, et al., "Optimum Current Duration for Capacitor-discharge Defibrillation of Canine Ventricles," J. Applied Physiology, Vol 27, p. 480, October, 1969.] Although the exact reason for this detrimental effect is not known, plausible speculations exist, with one possibility being that field heterogeneities cause arrhythmias in significantly large regions of the heart. [P. S Chen, et al., "The Potential Gradient Field Created by Epicardial Defibrillation Electrodes in Dogs," Circulation, Vol. 74, p. 626, September 1986.] A convenient way to eliminate the low-amplitude "tail" of a capacitor discharge is by switching, which is to say, simply opening the capacitor-load circuit after a predetermined time, or else when voltage has fallen to a particular value. For this reason, the time-truncated capacitor discharge has been extensively used after its effectiveness was first demonstrated. [J. C. Schuder, et al., "Transthoracic Ventricular Defibrillation in the Dog with Truncated and Untruncated Exponential Stimuli," IEEE Trans. Biom. Eng., Vol. BME-18, p. 410, November 1971.]

Two methods for specifying a time-truncated capacitor-discharge pulse in defibrillation systems have been extensively used. But neither method has involved systematic optimization of the pulse. Some manufacturers such as Medtronic in their PCD product simply specify pulse duration, although the physician can choose and adjust the value. A typical value might be a programmable duration of 7 ms. Other manufacturers such as Cardiac Pacemakers in their Ventak product specify the relative amount of voltage decline at the time of truncation, with a typical value of the decline being 65% of the initial voltage. It has become customary to use the term "tilt" to describe the relative amount of such voltage decline, expressed either as a decimal fraction or a percentage. In algebraic language, $$\text{tilt} = (V_{initial} - V_{final})/V_{initial}. \qquad \text{Eq.1}$$

As a specific illustration of prior-art practice, one can review a CPI system that uses a 140-microfarad capacitor for defibrillation. When used with large-area electrodes that typically yield a cardiac electrical resistance of 50 ohms, the system displays an RC time constant of 7 milliseconds. Using the specification of 65% tilt, one obtains a pulse duration of approximately 7 milliseconds, the RC time. But since one arbitrarily specifies the same tilt specification for cardioversion, and since using the same RC system leads to the same pulse duration, it follows that the final voltage of the cardioversion pulse at the time of truncation can be as low as 40 to 50 volts, depending upon the cardioversion energy chosen. In particular, for a 1-joule pulse from the CPI system, the trailing voltage is 43 volts. Clinical experience with cardioversion pulses having durations in this vicinity shows an effectiveness of only 50 to 80 percent.

In addition to the hazard of supplying such a low voltage to the heart, this prior art constitutes a waste of energy. In tachycardia, heart cells that must be reset are in the state of diastole, a task requiring less energy than resetting cells that are in systole, as in the case of ventricular fibrillation. This fact is reflected in the lower energies typically chosen for cardioversion, but permits a further reduction of the pulse duration without sacrificing effectiveness, and while eliminating the dangerous low-voltage tail from the cardioversion pulse.

A characteristic time associated with far-field diastolic stimulation using electrodes relatively remote from the heart is in the neighborhood of 1 millisecond. Hence the prior-art cardioversion pulses are dramatically longer than the optimum. The elucidation of this characteristic time employs the concept of "chronaxie", that requires some background explanation:

The foundation for defining such a characteristic time is a family of mathematical neurophysiological models for tissue stimulation going back to the turn of the century, with the first important such model having been developed by Weiss. [G. Weiss, "Sur la Possibilite de Rendre Comparable entre Eux les Appareils Suivant a l'Excitation Electrique," *Arch. Ital. de Biol.*, Vol. 35, p. 413, 1901.] He employed the ballistic-rheotome technique for pulse generation, wherein a rifle shot of known velocity is used to cut two wires in sequence, their spacing being set and measured. Cutting the first wire eliminated a short from a dc source, causing current to flow through the tissue under test, and cutting the second wire opened the circuit, terminating the pulse applied. Converting the electrical data into charge delivered by the pulse, Weiss found that the charge Q needed for stimulation was linearly dependent on pulse duration, d. Specifically, $$Q = k_1 + k_2 d. \qquad \text{Eq. 2}$$

Subsequently and similarly, the physiologist L. Lapicque collected substantial amounts of data on the amount of current required to for tissue stimulation, using constant-current pulses of various durations. [L. Lapicque, "Definition Experimentelle de l'excitabilite," *Proc. Soc. de Biol.*, Vol 77, p. 280, 1909.]

Lapicque established an empirical relationship between the current I and the pulse duration d, having the form $$I = K_1 + (K_2/d). \qquad \text{Eq. 3}$$

Note that multiplying this expression through by d yields an expression in charge rather than current, identically the equation given by Weiss. Thus $K_1 = k_1/d$ and $K_2 = k_2 d$.

Equation 3 of Lapique shows that the necessary current and the pulse duration are related by a simple hyperbola, shifted away from the origin by the amount of the constant term $K_1$. Hence the stimulating current required in a pulse of infinite duration is $K_1$, a current value Lapicque termed the rheobase. Shortening the pulse required progressively more current, and the pulse duration that required a doubling of current for excitation, or $2K_1$, he termed the chronaxie, $d_c$. Substituting $2K_1$ and $d_c$ into Eq. 3 in place of I and d, respectively, yields $$d_c = K_2/K_1. \qquad \text{Eq. 4}$$

Lapicque's model described cell stimulation, rather than defibrillation, but Bourland demonstrated that defibrillation thresholds in dogs and ponies followed the Lapicque model, provided average current is used in the exercise. [J. D. Bourland, W. Tacker, and L. A. Geddes, "Strength-Duration Curves for Trapezoidal Waveforms of Various Tilts for Transchest Defibrillation in Animals," *Med. Instr.*, Vol 12, p. 38 1978.] In a companion paper, the same workers showed that average current, $I_{ave}$, is a useful and consistent measure of defibrillation effectiveness for time-truncated pulses of a given duration through a substantial range of durations, from 2 to 20 milliseconds; in other words, so long as the exponential "tail" is eliminated, pulse effectiveness is not very dependant upon waveform details. [J. D. Bourland, W. Tacker, and L. A. Geddes, "Comparative Efficacy of Damped Sine Waves and Square Wave Current for Transchest Defibrillation in Animals," *Med. Instr.*, Vol. 12, p. 42, 1978.] The defibrillation chronaxie for the heart is usually between 2 milliseconds and 4 milliseconds, as is borne out by a substantial fund of published data. [See co-pending application by Kroll and Smith, *Optimal-Pulse Defibrillator*, Ser. No. 07/835,836, filed Feb. 18, 1992.] For cardioversion, the chronaxie is approximately 1 millisecond. The phrase "pulse duration set automatically by the system" differentiates from the prior art that can be programmed to a short pulse duration by the physician. The phrase "which is less than the pulse duration for defibrillation" differentiates from the rest of the prior art world, (CPI, Ventritex, etc.) who have a fixed cardioversion pulse duration equal to their defibrillation pulse duration.

SUMMARY OF THE INVENTION

The general purpose of the present invention is to provide a process for waveform optimization. It builds upon the models of Lapicque and Weiss, and the finding of Bourland. To do this, the present invention defines a "sufficiency ratio," the ratio of Bourland's ruling average current and the current needed for defibrillation according to the Lapicque model for a heart of a given $K_1$, rheobase current, and a given $K_2$, a charge. Algebraically, $$\text{Sufficiency ratio} = I_{ave}/(K_1 + K_2/d) \qquad \text{Eq. 5}$$

It is simply the ratio of Bourland's available therapeutic current (or the average current $I_{ave}$) to the current required according to the Lapicque formulation. Hence for a ratio of unity, the waveform of average current $I_{ave}$ and duration d will be able to defibrillate a heart characterized by $K_1$ and $K_2$. To review briefly, recall that the current $K_1$ and the charge $K_2$ characterize the sensitivity of particular tissue to electrical stimulation. The smaller these quantities are, the more sensitive is the tissue in question to electrical stimulation. The quotient of these two quantities yields a characteristic time, the chronaxie, which does not by itself indicate sensitivity or insensitivity.

Multiplying Eq. 5 through by the rheobase current $K_1$ yields an expression that, of course, has dimensions of amperes; noting from Eq. 4 that $K_1 d_c = K_2$, makes it possible to eliminate the heart-characterizing quantities $K_1$ and $K_2$ from this expression:

$$[I_{ave}/(1 + K_2/K_1 d)] = [I_{ave}/(1 + d_c/d)] \qquad \text{Eq. 6}$$

Thus, one has an expression in the two pulse-characterizing quantities $I_{ave}$ and d, and in one heart-characterizing quantity, $d_c$, the chronaxie time. Note that for an infinite pulse duration, this current simply equals the average current $I_{ave}$, but for a pulse of finite duration, it will be smaller than $I_{ave}$. This current, therefore, measures the effectiveness of a particular waveform in defibrillating a particular heart. For this reason the inventors have named it the effective current or $I_e$, so that the defining equation is $$I_e = I_{ave}/(1 + d_c/d). \qquad \text{Eq. 7}$$

Note further that $I_e$ would be the same as $I_{ave}$ if one had a zero value of chronaxie time, $d_c$. In this sense, Eq. 7 constitutes a correction from actual average current necessitated by the chronaxie phenomenon. The effective current $I_e$ can be expressed in several ways:

$I_e = [I_{ave} d/(d_c+d)] = [(\text{delivered charge})/(d_c+d)] = CV_i(\text{tilt ratio})/(d_c+d).$  Eq. 8

Applying this formulation to a prior-art system employing C=140 microfarad, tilt=0.65, $V_i$=125 volts, and an interelectrode resistance of R=50 ohms (for a pulse duration of about 7 milliseconds) yields an effective current of $I_e = [(140 \text{ F})(125 \text{ V})(0.65)/(1 \text{ ms}+7 \text{ ms})] = 1.42 \text{ A}.$  eq. 9

It is convenient to illustrate the kind of information obtainable from this analysis by using the hypothetical (and easy to calculate) case of a rectangular current pulse employed for cardioversion. With a current I delivered to the (cardiac) load resistance R, we can write the energy E of the pulse as $E = IRd,$  Eq. 10 so that $$I = \sqrt{(E/Rd)} = I_{ave}.$$  Eq. 11

The object, now, is to maximize the effective current $I_e$, which is given by $$I_e = \frac{I_{ave}}{1 + d_c/d} = \frac{\sqrt{E/Rd}}{1 + d_c/d}$$  Eq. 12 or, $$I_e \sqrt{\frac{E}{R}} \frac{\sqrt{\frac{1}{d}}}{1 + d_c/d} = \sqrt{\frac{E}{R}} \frac{\sqrt{d}}{d_c + d}$$  Eq. 13

Differentiating this expression with respect to d and equating the results to zero yields:

$d = d_c$  Eq. 14

Thus, for a truly rectangular pulse, the optimal duration is simply the chronaxie time. This result has intuitive appeal, because one is matching the pulse duration to the natural time constant of the cardiac system. This result is known in pacing [J. A. Pearce, et al., "Myocardial Stimulation with Ultrashort Duration Pulses", PACE, Vol. 5, p. 52, Janurary–Feburary 1982], and has been derived for defibrillation as well. It was, in fact, noted by Lapique. Hence, our result using the concept of effective current is consistent with prior knowledge.

It is further instructive to calculate the current in the hypothetical 1-joule rectangular pulse having a duration of 1 millisecond for comparison with the effective current obtained above for the prior art truncated capacitor-discharge pulse having a duration of 7 milliseconds. From Eq. 10, $$I = \sqrt{[(1 \text{ J})/(50 \text{ ohm})(1 \text{ ms})]} = 4.47 \text{ A}.$$  Eq. 15

Thus the 1-joule pulse in this example yields an effective current over three times greater than that of a 1-joule pulse of the prior art, illustrating the virtue of a short pulse in spite of the hypothetical nature of the waveform in the present example.

Given that a truncated capacitor-discharge pulse is used in real life, the next task is to optimize such a pulse for cardioversion. A capacitor C will be charged to a voltage $V_i$ and discharged into a cardiac load resistance R, with time truncation to yield a pulse duration d. The capacitor value has been chosen with an eye to high-energy defibrillation. This fixed capacitor will be charged to a fixed voltage, resulting in the storage of a fixed energy in the capacitor. Neglecting converter losses, this energy will equal the energy drawn from the battery. That is, because it is not practical to recover energy left in the capacitor after a truncated pulse is delivered, it is the energy stored in the capacitor initially (rather than the energy delivered) that is relevant in determining how to budget battery energy among the pacing function, the cardioversion function with multiple shocks, and the defibrillation function, also with multiple shocks. The first challenge is to maximize the effective current $I_e$ for a given energy stored initially in the capacitor.

Because the waveform is a declining exponential function, and given that $RC = \tau$, the system time constant, tilt as a decimal fraction can be written as follows:

$\text{tilt} = 1 - \exp(-d/\tau)$  Eq. 16

Combining this expression and Eq. 8 yields $I_e = CV_i[1 - \exp(-d/\tau)]/(d_c+d).$  Eq. 17

It is clear the $I_e$ vanishes at both extremes of d, so the intermediate extremum must be a maximum, defining explicitly the optimum waveform that can be achieved by varying pulse duration with a particular average current. To determine this optimum pulse duration, set $$\frac{dI_e}{dd} = CV_i \frac{(d + d_c)(e^{-t/t}/t) - (1 - e^{-d/t})}{(d = d_c^2)} = 0$$  Eq. 18

Hence, $$\frac{d + d_c}{t} e^{-d/t} - 1 + e^{-d/t} = \frac{d_c = d}{t} + 1e^{-d/t} - 1 = 0$$  Eq. 19

Using the system time constant=RC for normalization yields $z = d/\tau$  Eq. 20 and $= d/\tau$  Eq. 21

Using these definitions, $(z+\alpha+1)[\exp(-z)]-1=0.$  Eq. 22

Next multiply through by $-e^{-z}$ to obtain the simplified equation whose root is:

$[\exp(-z)]-z-\alpha-1=0.$  Eq. 23

Because the equation is transcendental, it cannot be solved in closed form, so define the function on the left-hand side as f(z) and the first approximation for its root as $z_0$. The Newton-Raphson method gives an approximate value for the root as $z' = z_0 - f(z_0)/f'(z_0).$  Eq. 24

Experience shows that waveforms with a tilt of about 65% are effective, and this corresponds to d=τ, or $z_0=1$. Hence an appropriate approximate root is $$z' = 1 - \frac{e - 1 - a - 1}{e - 1} = \frac{1 + d}{e - 1}. \quad \text{Eq. 25}$$

Denormalization yields $$d = (\tau + d_c)/(e-1) \quad \text{Eq. 26}$$

for the approximate optimum value of pulse duration d as a function of chronaxie $d_c$ and system time constant τ. Carrying through the optimization numerically shows that this estimate is valid within 0.2% for typical values of R, C, and $d_c$. Even for extreme values of these system and heart parameters, the approximate value of optimum duration produces a value for the current $I_e$ that is within 2% of the optimum. Since (e−1)=1.72, the optimum pulse duration is approximately (and somewhat larger than) the average of the system's time constant and the heart's characteristic time $d_c$. In other words, the optimum pulse duration is a compromise between the two characteristic times involved.

To illustrate the application of this analysis, let us return to the case of the prior-art system employing C=140 microfarads, $V_i$=125 volts, and an interelectrode resistance of R=50 ohms. We now determine the optimal pulse duration d for this case, describing a preferred embodiment of the present invention in the process. From Eq. 26, recalling that d=1millisecond for cardioversion, $$d=[(7\text{ms}+1\text{ms})/(e-1)]=4.65\text{ms}. \quad \text{Eq. 27}$$

For this pulse duration, tilt amounts to 49%, or 0.49. Hence the effective current from Eq. 8, once more, is $$I_e=[(140\text{F})(125\text{V})(0.49)/(1\text{ms}+4.65\text{ms})]=1.52\text{A}. \quad \text{Eq. 28}$$

This constitutes an increase over the prior-art value (1.42 ampere) for the same system in spite of the fact that less energy is delivered by the optimal pulse with its shorter duration. And the optimal pulse brings the further benefit of eliminating the lingering low-voltage portions of the pulse that can lead to ventricular fibrillation. The optimized pulse has a final voltage of $V_f$=64 V, while for the prior-art pulse, the value is $V_f$=44 V. The further advantage is that the 64-V value exists at a time less then 5 ms, while the 44-V value of the prior art exists at 7 ms. The delivery of an optimized pulse such as this for cardioversion is one of the essences of the present invention.

In addition to the advantages just cited, there are further benefits to be gained by maximizing the quotient of effective current by pulse energy. Diminished energy reduces the inevitable damage to myocardial tissue. Even further, it diminishes pain. Thus, an impressive set of betterments flow from the short cardioversion pulse of the present invention.

The discussion thus far has addressed the issue of optimization for the case where energy initially stored in the battery is held constant. There is, however, a different problem that is worth addressing. That is, the case where delivered energy is held constant. This implies a higher initial voltage $V_i$ as pulse duration shrinks. But, this further involves a diminished tilt, and hence, a more nearly rectangular pulse. Conceding that increased amounts of energy must be stored in the battery initially for each such pulse, and that energy remaining in the capacitor cannot be recovered, and hence is wasted, we nonetheless believe this line of inquiry to be worthwhile.

Note first that going from a 7-ms conventional pulse to a 1-ms pulse reduces tilt from about 65% to about 14%, as is illustrated in FIG. 6. Because this is an excellent approximation to rectangular form, we receive the benefit of the kind of pulse connected with the calculation in Eq. 15. Further, as demonstrated in Eq. 14, the optimal duration of a rectangular pulse is simply the chronaxie, $d_c$. Thus, the insights in the present invention permit us to specify conditions adjacent to the optimal extreme. An exact solution involving the short pulse of FIG. 6 yields an optimal duration only slightly larger than the chronaxie, and having an effective current within 1% of that obtained by simply using the chronaxie.

Cardioversion can be accomplished by using a monophasic wave, such as that illustrated in FIGS. 1 and 2. The first shows a preferred embodiment of the present invention, with the pulse properties specified in terms of initial voltage and pulse duration; the second employs initial voltage and tilt, producing the same result in this case. A simplified representation of a circuit for generating such a monophasic pulse is illustrated in FIG. 3. But cardioversion, like defibrillation, can be accomplished by means of a multiphasic pulse as well as a monophasic pulse. An example of a multiphasic pulse is the biphasic pulse illustrated in FIG. 4, and the corresponding circuit is shown in FIG. 5. In the biphasic case, the present method is used to fix the duration of the first phase, and then one usually lets the duration of the second phase equal a fraction of that determined to be optimal for the first.

One significant aspect and feature of the present invention is a cardioversion waveform of optimum duration for the case of fixed stored energy.

Another significant aspect and feature of the present invention is a pulse duration that comprehends the time constant of the pulse-delivery system, RC, and the heart's characteristic time, the chronaxie, $d_c$.

Still another significant aspect and feature of the present invention is a pulse duration that is approximately an average of the system time constant, RC, and the heart's characteristic time, the chronaxie, $d_c$.

Yet another significant aspect and feature of the present invention is maximizing the quotient of cardioversion-pulse effectiveness by pulse energy.

An additional significant aspect and feature of the present invention is the use of a cardioversion pulse of optimum duration in a monophasic waveform.

A further significant aspect and feature of the present invention is the use of a cardioversion pulse of optimum duration in the first phase of a biphasic waveform.

A still further significant aspect and feature of the present invention is the use of a cardioversion pulse of optimum duration in the first phase of a biphasic waveform, with the second phase having a duration that is equal or smaller.

An additional significant aspect and feature of the present invention is that the short pulse prescribed in the case of fixed delivered energy approximates a rectangular pulse.

Having thus described embodiments and features of the present invention, it is a principal object of the pres- ent invention to achieve the optimum duration in a cardioversion waveform for the case of fixed stored energy.

An object of the present invention is delivery of a cardioversion pulse of improved effectiveness.

Another object of the present invention is to employ a cardioversion-pulse duration that comprehends the system time constant, RC, and the heart's characteristic time, the chronaxie, $d_c$.

Another object of the present invention is to employ a cardioversion-pulse duration that is approximately an average of the system time constant, RC, and the heart's characteristic time, the chronaxie, $d_c$.

An additional object of the present invention is to employ a cardioversion pulse of optimum duration in a monophasic waveform.

A still further object of the present invention is to employ a cardioversion pulse of optimum duration in at least one phase of a biphasic waveform.

Yet another object of the present invention is to employ a defibrillation pulse of optimum duration in one phase of a biphasic waveform, with the other phase having a duration that is equal or smaller.

Yet an additional object of the present invention is maximizing the quotient of effective current in a cardioversion pulse by pulse energy.

Another object of the present invention is to diminish patient pain.

Yet another object of the present invention minimizing damage to myocardial tissue.

Still another object of the present invention is to provide a cardioversion pulse in the case of fixed delivered energy that approximates a rectangular pulse.

BRIEF DESCRIPTION OF THE DRAWINGS

Other objects of the present invention and many of its attendant advantages will be readily appreciated as the invention becomes better understood by reference to the following descriptions, when considered in connection with the accompanying drawings in which like reference numerals designate like parts throughout the figures thereof, and wherein.

DETAILED DESCRIPTION OF THE PREFERRED EMBODIMENTS

Figure 1:
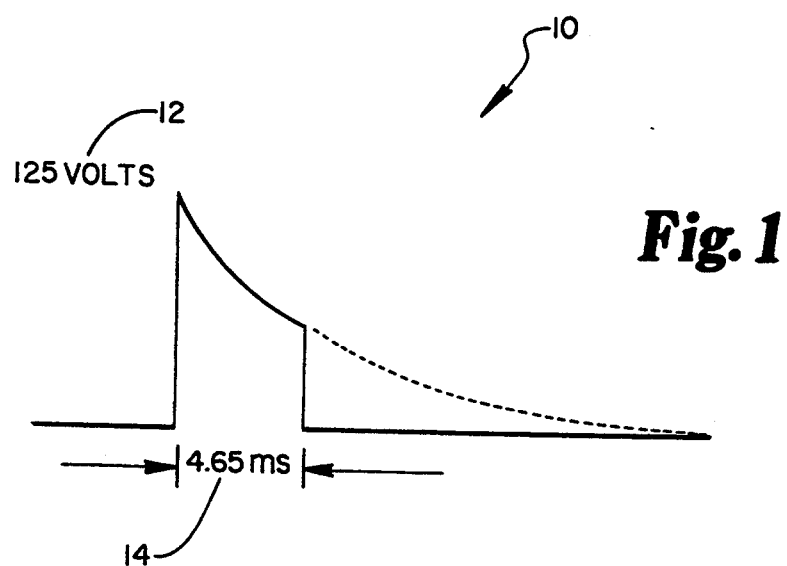
FIG. 1 illustrates a preferred-embodiment monophasic pulse for cardioversion using the present invention.

FIG. 1 illustrates the waveform 10 of a preferred-embodiment monophasic pulse for cardioversion of the present invention, specified by means of an initial voltage 12 and a duration 14.

Figure 2:
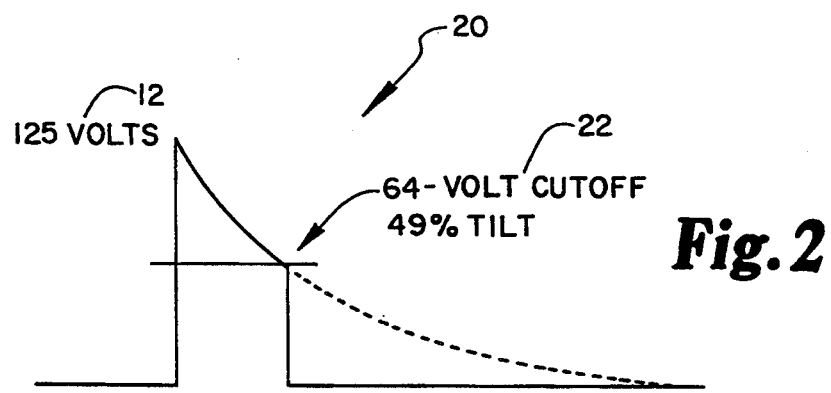
FIG. 2 illustrates the same preferred-embodiment monophasic pulse of the present invention, but with different specification.

FIG. 2 illustrates the waveform 20 of a preferred-embodiment monophasic pulse for cardioversion of the present invention, specified by means of an initial voltage 12 and a tilt 22.

Figure 3:
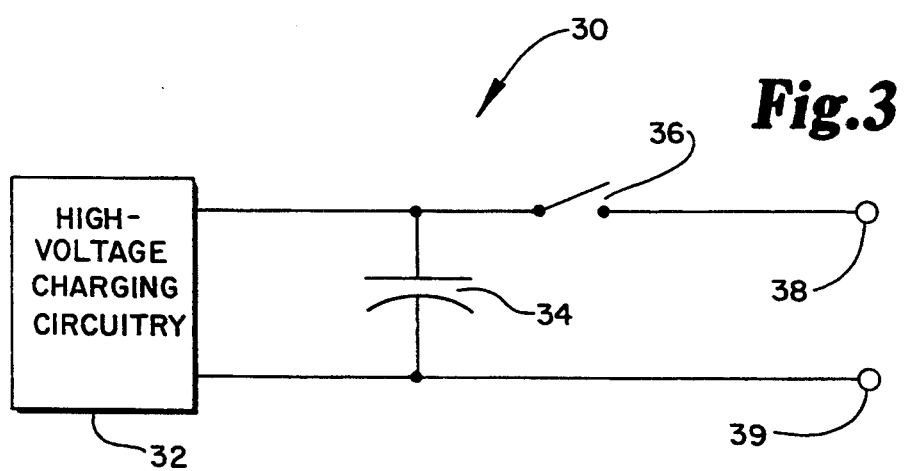
FIG. 3 illustrates a simplified representation of a circuit for generating the monophasic pulse of FIGS. 1 and 2.

FIG. 3 illustrates a representation 30 of an electrical circuit for generating the monophasic pulse of FIGS. 1 and 2, including high-voltage charging circuitry 32 for the capacitor 34, and a switch 36 that is closed to deliver the pulse to the cardiac electrodes 38 and 39.

Figure 4:
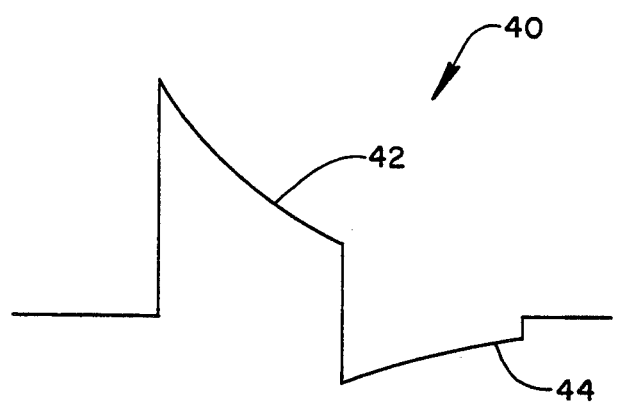
FIG. 4 illustrates an example of a biphasic pulse for cardioversion of the present invention.

FIG. 4 illustrates the waveform 40 of an example of a biphasic pulse for cardioversion of the present invention, including a first phase 42 and a contiguous second phase 44.

Figure 5:
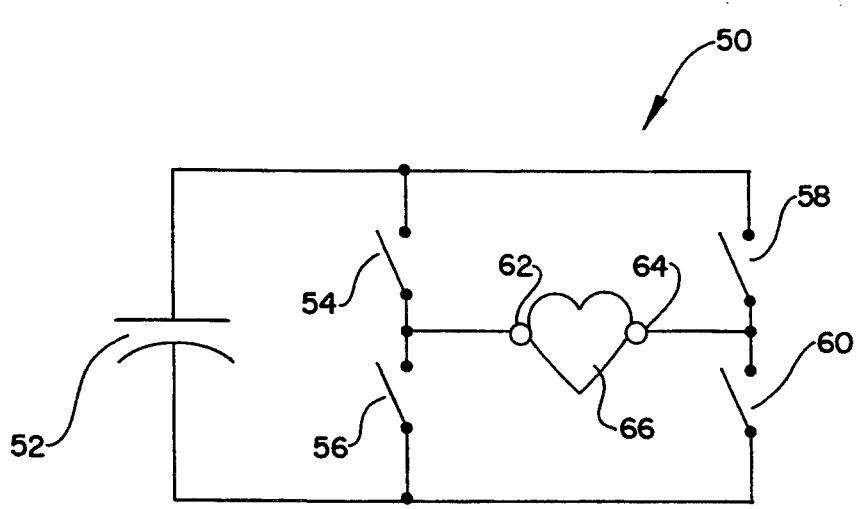
FIG. 5 constitutes a simplified representation of a circuit for generating the biphasic pulse of FIG. 4; and, FIG. 6 illustrates defibrillation and cardioversion waveforms of the prior art and a cardioversion waveform for one embodiment of the present invention.

FIG. 5 illustrates a representation 50 of an electrical circuit for generating the biphasic waveform 40 of FIG. 4, including a capacitor 52, the four switches 54, 56, 58, and 60 that are able to reverse polarity in going from the first phase 42 of FIG. 4 to the second phase 44 of FIG. 4 for purposes of delivering the biphasic waveform 40 of FIG. 4 to the cardiac electrodes 62 and 64 positioned on or near the heart 66.

Figure 6:
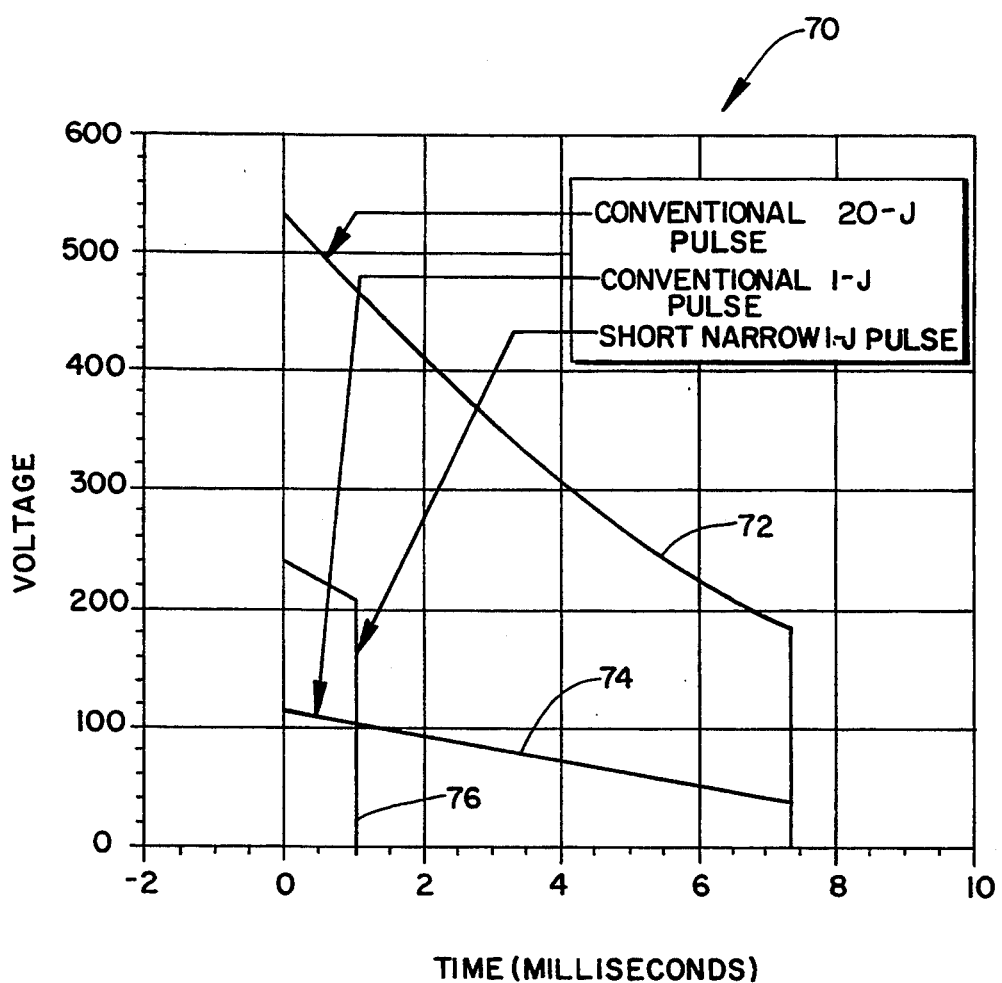

FIG. 6 illustrates a set 70 of voltage-versus-time waveforms, including the defibrillation waveform 72 of the prior art, the cardioversion waveform 74 of the prior art, and the cardioversion waveform 76 for one preferred embodiment of the present invention.

MODE OF OPERATION

The model that is developed in the present invention is based upon the pioneering neurophysiological models of Lapicque and Weiss. The present model determines mathematically the optimum pulse duration, d, for a truncated capacitor-discharge waveform employed for cardioversion. It comprehends the system time constant, RC, where R is tissue resistance and C is the value of the capacitor being discharged, and also the heart's cardioversion chronaxie, $d_c$, defined by Lapicque, which is a characteristic time associated with the stimulation of heart tissue.

The present model and analysis find the optimum pulse duration for the case of fixed energy stored to be roughly the average of RC and $d_c$, appreciably smaller than the value employed in the prior art. The optimized-pulse prescription of this invention can be applied to a monophasic waveform, or to the first phase of a biphasic waveform. In the latter case, when it is applied to the first phase, the second phase can be specified to have equal or lesser duration than the first.

When energy delivered to the heart is taken to be constant, and the waveform is optimized on that basis, then the pulse duration approximates the chronaxie of the myocardial tissue, and the waveform approximates a rectangular pulse.

Table 1 illustrates a table of pulse width over time versus delivered energy.

TABLE 1

| Delivered Energy | Pulse width (ms) → | | |
|---|---|---|---|
| | 0.5–3 | 1–6 | ≧6 |
| >5 J | | | conventional defibrillation |
| 0.5–5 J | short-pulse cardioversion which minimizes delivered energy | short-pulse cardioversion which minimizes stored energy | conventional cardioversion |

Various modifications can be made to the present invention without departing from the apparent scope hereof.

We claim:

1. An improved implantable apparatus for producing a cardioversion waveform of less than about 5 Joules to be delivered to a plurality of implanted electrodes in a human patient the implantable apparatus including capacitor means for storing a preselected amount of electrical energy for the cardioversion waveform, high voltage charging circuit means for charging the capacitor means to the preselected amount of electrical energy, and switch means for selectively controlling a time-truncated discharge of the capacitor means through the plurality of electrodes in response to a means for sensing of the cardiac arrhythmia, the improvement comprising:

the cardioversion waveform comprising at least one electrical pulse having a predetermined optimum pulse duration of between 0.5 ms and 6.0 ms.

2. The improved apparatus of claim 1 wherein the optimum pulse duration is the sum of:

a first value derived from a first predetermined percentage of an RC time constant, with R being an inter-electrode resistance value between the plurality of electrodes and C being an effective capacitance value of the capacitor means; and a second value derived from a second predetermined percentage of a cardioversion chronaxie value.

3. The improved apparatus of claim 2 wherein the first and second predetermined values are between 0.4 and 0.8.

4. The improved apparatus of claim 1 wherein the optimum pulse duration is selected to be between 4.0 and 5.0 ms so as to reduce a stored energy requirement for delivering the cardioversion waveform and thereby decrease an overall displacement volume of the implantable apparatus.

5. The improved apparatus of claim 4 wherein the optimum pulse duration is selected to be between 4.5 and 04.8 ms.

6. The improved apparatus of claim 1 wherein the optimum pulse duration is selected to be a percentage tilt decay between an initial voltage value and a final voltage value where the percentage tilt is between about 34% and 64%.

7. The improved apparatus of claim 6 wherein the percentage tilt is between about 48% and 50%.

8. The apparatus of claim 1 wherein the optimum pulse duration is determined for a first pulse of a multiple pulse cardioversion waveform.

9. The apparatus of claim 1 wherein the optimum pulse duration is determined for a first phase of a multiphasic pulse cardioversion waveform.

10. The improved apparatus of claim 1 wherein the optimum pulse duration is a time period that is shorter than a first time constant that is a system time constant, RC, of the apparatus, where R is an inter-electrode resistance of the heart of the human patient and C is an effective capacitance of the capacitor means, and longer than a second time constant that is an average cardioversion chronaxie value of the heart of the human patient.

11. The apparatus of claim 1 wherein the predetermined optimum pulse duration is optimized for an amount of the preselected amount of electrical energy in the capacitor means that is delivered to the electrodes such that the predetermined pulse duration of the cardioversion waveform essentially matches an average cardioversion chronaxie value of the heart of the human patient, whereby an overall pain level of the cardioversion waveform is reduced.

12. The improved apparatus of claim 1 wherein the optimum pulse duration is selected to be between 0.5 ms and 3.0 ms so as to decrease pain induced in the human patient by the cardioversion waveform.

13. The improved apparatus of claim 12 wherein the optimum pulse duration is selected to be between 0.8 and 1.2 ms.

14. The improved apparatus of claim 1 wherein the optimum pulse duration is selected to be a percentage tilt decay between an initial voltage value and a final voltage value where the percentage tilt is between about 5% and 20%.

15. The improved apparatus of claim 14 wherein the percentage tilt is between about 12% and 16%.

16. An improved method for selecting an optimal pulse duration for operating an implantable cardioverter defibrillator device connected to a plurality of implanted electrodes located in a human patient to treat a cardiac arrhythmia, the implantable cardioverter defibrillator device being a self-contained human implantable device including a pulse-generating capacitor for storing an electrical charge, a battery for internally charging the pulse-generating capacitor, and a controller for selectively discharging the electrical charge in the pulse-generating capacitor through the plurality of electrodes in response to a sensing of a cardiac arrhythmia in the human patient, the improved method comprising the steps of:

(a) selecting a predetermined optimum pulse duration for a time-truncated cardioversion waveform that is between 0.5 ms and 6.0 ms; and (b) setting the cardioverter defibrillator device to deliver the time-truncated cardioversion waveform such that the cardioversion waveform comprises at least one electrical pulse of less than about 5 Joules.

17. The improved method of claim 16 wherein the optimum pulse duration is the sum of:

a first value derived from a first predetermined percentage of an RC time constant, with R being an inter-electrode resistance value of the plurality of electrodes and C being an effective capacitance value of the capacitor; and a second value derived from a second predetermined percentage of a cardioversion chronaxie value.

18. The improved method of claim 17 wherein the first and second predetermined values are between 0.4 and 0.8.

19. The improved method of claim 16 wherein the optimum pulse duration is selected to be between 4.0 and 5.0 ms so as to reduce a stored energy requirement for delivering the cardioversion waveform and thereby decrease an overall displacement volume of the implantable device.

20. The improved method of claim 19 wherein the optimum pulse duration is between about 4.5 and 4.8 ms.

21. The improved method of claim 16 wherein the optimum pulse duration is measured by a percentage tilt decay between an initial voltage value and a final voltage value where the percentage tilt is between about 34% and 64%.

22. The improved method of claim 21 wherein the percentage tilt is between about 48% and 50%.

23. The method of claim 16 wherein the optimum pulse duration is determined for a first pulse of a multiple pulse cardioversion waveform.

24. The method of claim 16 wherein the optimum pulse duration is determined for a first phase of a multiphasic pulse cardioversion waveform.

25. The improved method of claim 16 wherein the optimum pulse duration is a time period that is shorter than a first time constant that is a system time constant, RC, of the implantable cardioverter defibrillator, where R is an inter-electrode resistance of the heart of the human patient and C is an effective capacitance of the capacitor and longer than a second time constant that is an average cardioversion chronaxie value of the heart of the human patient.

26. The improved method of claim 16 wherein the optimum pulse duration is selected to be between 0.5 ms and 3.0 ms so as to decrease pain induced in the human patient by the cardioversion waveform.

27. The improved method of claim 26 wherein the optimum pulse duration is between about 0.8 and 1.2 ms.

28. The improved method of claim 16 wherein the optimum pulse duration is measured by a percentage tilt decay between an initial voltage value and a final voltage value where the percentage tilt is between about 5% and 20%.

29. The improved method of claim 28 wherein the percentage tilt is between about 12% and 16%.

30. An improved implantable cardioverter defibrillator apparatus for producing a cardioversion waveform of less than about 5 Joules and a defibrillation waveform of greater than about 5 Joules, both of which are to be delivered to at least two or more implanted electrodes in a human patient the implantable apparatus including capacitor means for storing a preselected amount of electrical energy for the cardioversion waveform, high voltage charging circuit means for charging the capacitor means to the preselected amount of electrical energy, and switch means for selectively controlling a time-truncated discharge of the capacitor means through the plurality of electrodes in response to a means for sensing of the cardiac arrhythmia, the improvement comprising:

the switch means including:
means for delivering the cardioversion waveform comprising at least one electrical pulse and having a predetermined pulse duration, and
means for delivering the defibrillation waveform comprising at least one electrical pulse and having a second predetermined pulse duration,
such that the predetermined pulse duration of the cardioversion waveform is less than the second predetermined pulse duration of the defibrillation waveform.

31. An improved method for operating an implantable cardioverter defibrillator for producing a cardioversion waveform of less than about 5 Joules and a defibrillation waveform of greater than about 5 Joules, both of which are to be delivered to a plurality of implanted electrodes in a human patient in response to a sensing of a cardiac arrhythmia in the patient, the implantable cardioverter defibrillator device being a self-contained human implantable device including pulse-generating capacitor system for storing an electrical energy, a battery for internally charging the pulse-generating capacitor system, and a controller for selectively discharging the electrical energy in the pulse-generating capacitor through the plurality of electrodes, the improved method comprising the steps of:

(a) in response to a tachycardia arrhythmia, selectively delivering from the electrical energy stored in the capacitor system in the implantable cardioverter defibrillator to the plurality of implanted electrodes a time-truncated cardioversion waveform comprising at least one electrical pulse and having a predetermined pulse duration, and (b) in response to a fibrillation arrhythmia, selectively delivering from the electrical energy stoed in the implantable cardioverter defibrillator to the plurality of implanted electrodes a time-truncated defibrillation waveform comprising at least one electrical pulse and having a second predetermined pulse duration, such that the predetermined pulse duration of the cardioversion waveform is less than the second predetermined pulse duration of the defibrillation waveform.

* * * * *